US00PP08953P

United States Patent [19]

McGredy

[11] Patent Number: Plant 8,953

[45] Date of Patent: Oct. 25, 1994

[54] HYBRID TEA ROSE PLANT NAMED MACHORO

[75] Inventor: Sam McGredy, Auckland, New Zealand

[73] Assignee: DeVor Nurseries, Inc., Watsonville, Calif.

[21] Appl. No.: 148,825

[22] Filed: Nov. 4, 1993

[51] Int. Cl.[5] ..... A01H 5/00

[52] U.S. Cl. ..... Plt./20

[58] Field of Search ..... Plt. 20, 21

*Primary Examiner*—Howard J. Locker

*Attorney, Agent, or Firm*—Christie, Parker & Hale

[57] ABSTRACT

A new hybrid tea rose plant producing red flowers.

1 Drawing Sheet

SUMMARY OF THE INVENTION

The present invention relates to a new and distinct variety of rose plant of the hybrid tea rose class which was originated by my crossing as seed parent the variety known as 'Macspeego' and as pollen parent the variety known as 'Macbucpal'. The varietal denomination of this new rose is 'Machoro'.

Among the novel characteristics possessed by this new variety which distinguish it from its parents and all other varieties of which I am aware are its attractive red flowers with ruffled petal edge.

Blooms of 'Machoro' are larger than blooms of both its parents and are less fragrant than both its parents.

Asexual reproduction by budding of the new variety as performed in Watsonville, Calif. shows that the foregoing and other distinguishing characteristics come true to form and are established and transmitted through succeeding propagations.

BRIEF DESCRIPTION OF ILLUSTRATION

The accompanying illustration shows typical specimens of the vegetative growth and flowers of the new variety in different stages of development and depicted in color as nearly true as it is reasonably possible to make the same in a color illustration of this character.

DETAILED DESCRIPTION OF THE NEW VARIETY

Parentage: Seedling. Seed parent: 'Macspeego'. Pollen parent: 'Macbucpal'.

Class: Hybrid tea.

The following is a detailed description of my new variety, of specimens grown outdoors in Watsonville, Calif. in the month of June. The color terminology used is in accordance with The Royal Horticultural Society Colour Chart (RHSCC), and refers to plate numbers in the aforementioned color chart. Phenotypic expression may vary depending on light, environmental and cultural conditions.

FLOWER

Blooming habit: Continuous.

A. Bud:

(1) *Size.*—Small.

(2) *Form.*—Pointed with ovoid base.

(3) *Color.*—Before sepals divide, bud color is green with near 185A.

(4) *Sepals.*—Sepals cover bud when tight then spread upon opening of bud, after which they reflex. Color: Near 144A on outside; near 148C at edges with near 144D in center, on inside.

(5) *Peduncle.*—Length: About 5–6 cm. Aspect: Straight. Strength: Erect, sturdy. Color: Near 138A.

(6) *Bracts.*—Generally not present.

B. Bloom:

(1) *Size.*—Average size when fully expanded — about 11–12 cm.

(2) *Borne.*—Singly, one to a stem and in sprays of 2–4 blooms.

(3) *Form.*—Imbricated from a balled center becoming ruffled at maturity.

(4) *Petalage.*—Number of petals under normal conditions — about 40.

(5) *Color.*—After sepals fall and petals unfurl, predominant flower color viewing top surface of outer petals is near 46A to 46B and as flower opens to $\frac{1}{3}$–$\frac{1}{2}$ open stage, flower color is near 46A to 47A. Undersurface of outer petals is somewhat lighter. Color at point of petal attachment is near 3A. Color of bloom upon aging lightens and general tonality at a distance becomes red scarlet.

C. Petals:

(1) *Texture.*—Thick.

(2) *Appearance.*—Inside velvety; outside slightly satiny.

(3) *Form.*—Elliptic with slightly ruffled edges.

(4) *Arrangement.*—Imbricated and slightly balled in center.

(5) *Petaloids.*—Many.

(6) *Fragrance.*—Slight to none.

(7) *Lasting quality.*—Up to 2 weeks on plant and 7–10 days as cut flower.

(8) *Persistence.*—Petals persist.

REPRODUCTIVE ORGANS

A. Stamens:

(1) *Arrangement.*—Not regularly arranged.

(2) *Anthers.*—Color — near 14D.

(3) *Filaments.*—Color — near 58A.

(4) *Pollen.*—Color — near 174C.

B. Pistils (1) *Styles.*—Bunched, uneven.

(2) *Stigmas.*—Color — near 19B.

Characteristics of Hips: Not observed.

PLANT

A. Form: Upright.

B. Growth: Vigorous, uniform branching; height attained about 178 cm at first season.

C. Foliage: Compound 3, 5 and 7 leaflets.

(1) *Size.*—Medium.

(2) *Quantity.*—Abundant.

(3) *Color.*—Upper side — near 147A. Under side — near 147B.

(4) *Shape.*—Ovate.

(5) *Texture.*—Leathery to slightly leathery.

(6) *Edge.*—Serrate.

(7) *Serration.*—Denticulate.

(8) *Leaf Stem.*—Color — medium green.

(9) *Stipules.*—Thin, narrow, slightly bearded, curling downward.

(10) *Rachis.*—Prickles-slight to none.

(11) *Petioles.*—Top near 53B; underside near 146B.

(12) *Auricle.*—Long, pointed.

(13) *Resistance to disease.*—Very good to blackspot; fair to mildew; very good to rust.

D. Wood (1) *New wood.*—Color — new shoots near 187A. Bark — smooth.

(2) *Old wood.*—Color — near 147A. Bark — smooth.

E. Flower stem: About 60-90 cm from last cut.

F. Thorns:

(1) *Thorns.*—Quantity (main stalk) — ordinary. On laterals from stalk — ordinary. Form — slightly curved downward. Length — medium. Color — near 187A when young. Position — irregular.

(2) *Prickles.*—Average.

G. Winter hardiness: Winter-hardy in Watsonville, no die-back.

I claim:

1. A new and distinct variety of rose plant of the hybrid tea rose class, substantially as shown and described.

* * * * *

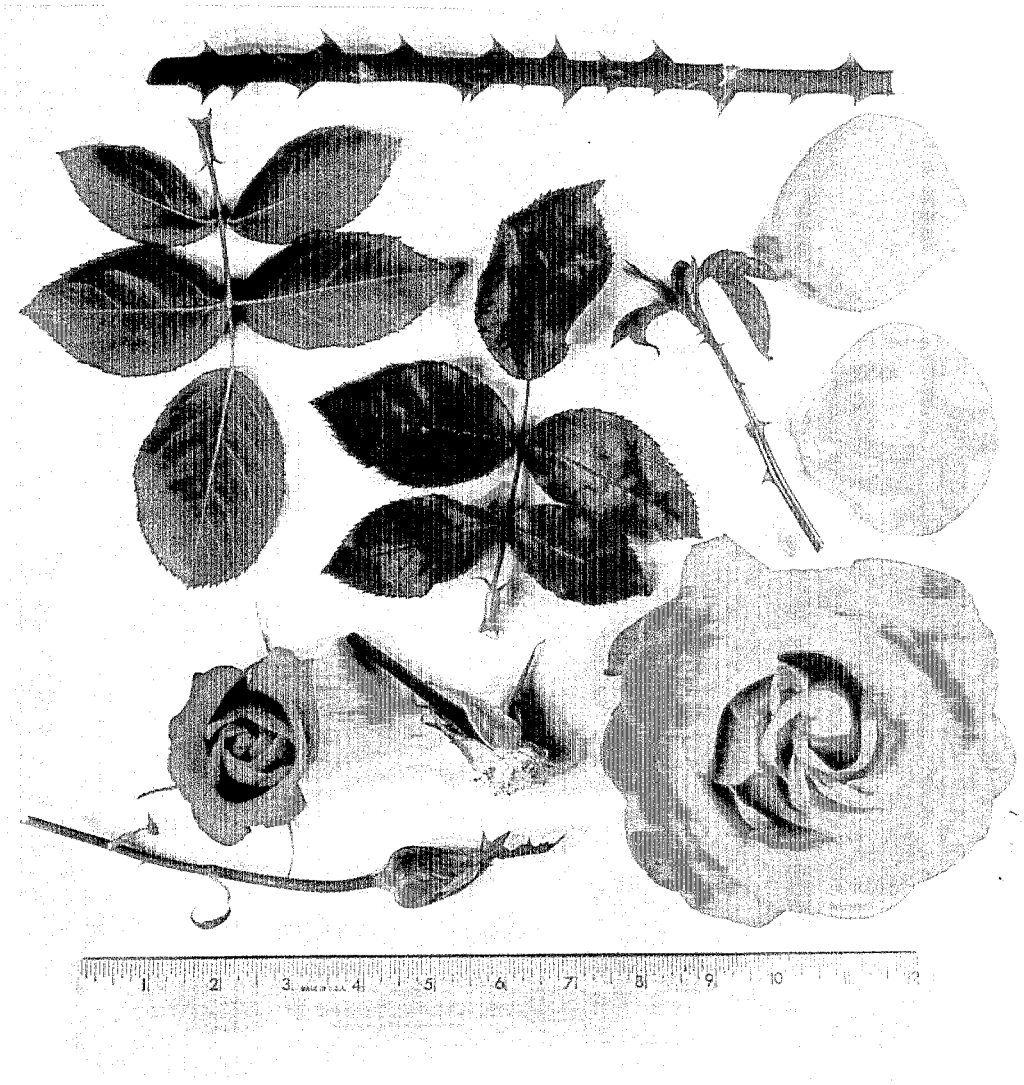

UNITED STATES PATENT AND TRADEMARK OFFICE

CERTIFICATE OF CORRECTION

PATENT NO. : Plant 8,953

DATED : October 25, 1994

INVENTOR(S) : Sam McGredy

It is certified that error appears in the above-indentified patent and that said Letters Patent is hereby corrected as shown below:

On the Title Page

After [58] insert the following reference:

-- [56] Reference Cited
U.S. PATENT DOCUMENT
P.P. 3,163 5/1972 Swim et al. ..Plt.20 --.

Signed and Sealed this

Eleventh Day of April, 1995

*Attest:*

*Attesting Officer*

BRUCE LEHMAN

*Commissioner of Patents and Trademarks*